United States Patent [19]

Peterson

[11] Patent Number: 5,794,695

[45] Date of Patent: Aug. 18, 1998

[54] METHOD AND APPARATUS FOR GATHERING AND PREPARING LIQUID SAMPLES FOR ANALYSIS

[76] Inventor: Roger Peterson, Rt 1 Box 316, Sweeng, Tex. 77480

[21] Appl. No.: 692,018

[22] Filed: Aug. 2, 1996

[51] Int. Cl.$^6$ ...................................................... E21B 49/08
[52] U.S. Cl. ................................................ 166/264; 166/68
[58] Field of Search .............................. 166/264, 68, 105, 166/64, 370, 267

[56] References Cited

U.S. PATENT DOCUMENTS

| | | | |
|---|---|---|---|
| Re. 34,754 | 10/1994 | Dickinson et al. | 166/64 |
| 4,585,060 | 4/1986 | Bernardin et al. | 166/64 |
| 4,669,554 | 6/1987 | Cordry | 166/264 X |
| 5,050,386 | 9/1991 | Krieg et al. | 62/45.1 |
| 5,146,998 | 9/1992 | Cordry et al. | 166/264 X |
| 5,189,909 | 3/1993 | Oike et al. | 166/264 X |
| 5,238,060 | 8/1993 | Niehaus et al. | 166/68 |
| 5,327,981 | 7/1994 | Morgan | 166/162 X |

*Primary Examiner*—Frank Tsay
*Attorney, Agent, or Firm*—Gunn & Associates, P.C.

[57] ABSTRACT

The invention is directed toward apparatus and methods for gathering and preparing liquid samples for analysis for elements or compounds within the liquid samples. Although applicable to a variety of liquids and to a variety of elements or compounds, the preferred embodiment of the invention is directed toward the gathering and pretreating of water samples for tritium analysis. This disclosure is further directed toward apparatus and methods for the gathering or collecting of water samples from underground formations penetrated by a borehole, or collecting water samples at varying depths in surface canals, ponds, and the like. The invention is particularly suited for monitoring water in the vicinity of nuclear manufacturing, fabrication and disposal facilities for tritium contamination of ground waters.

21 Claims, 3 Drawing Sheets

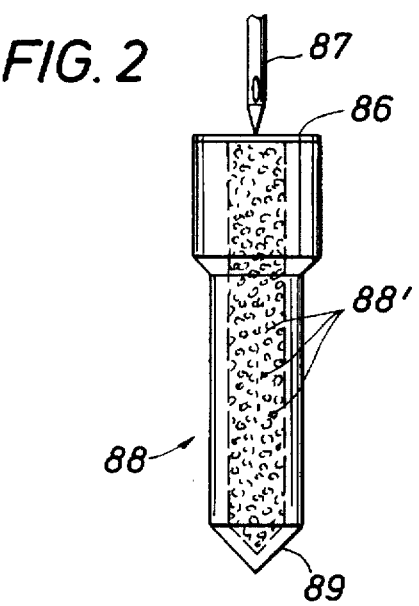
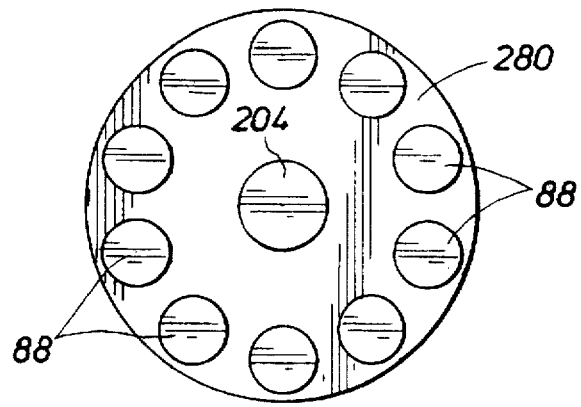
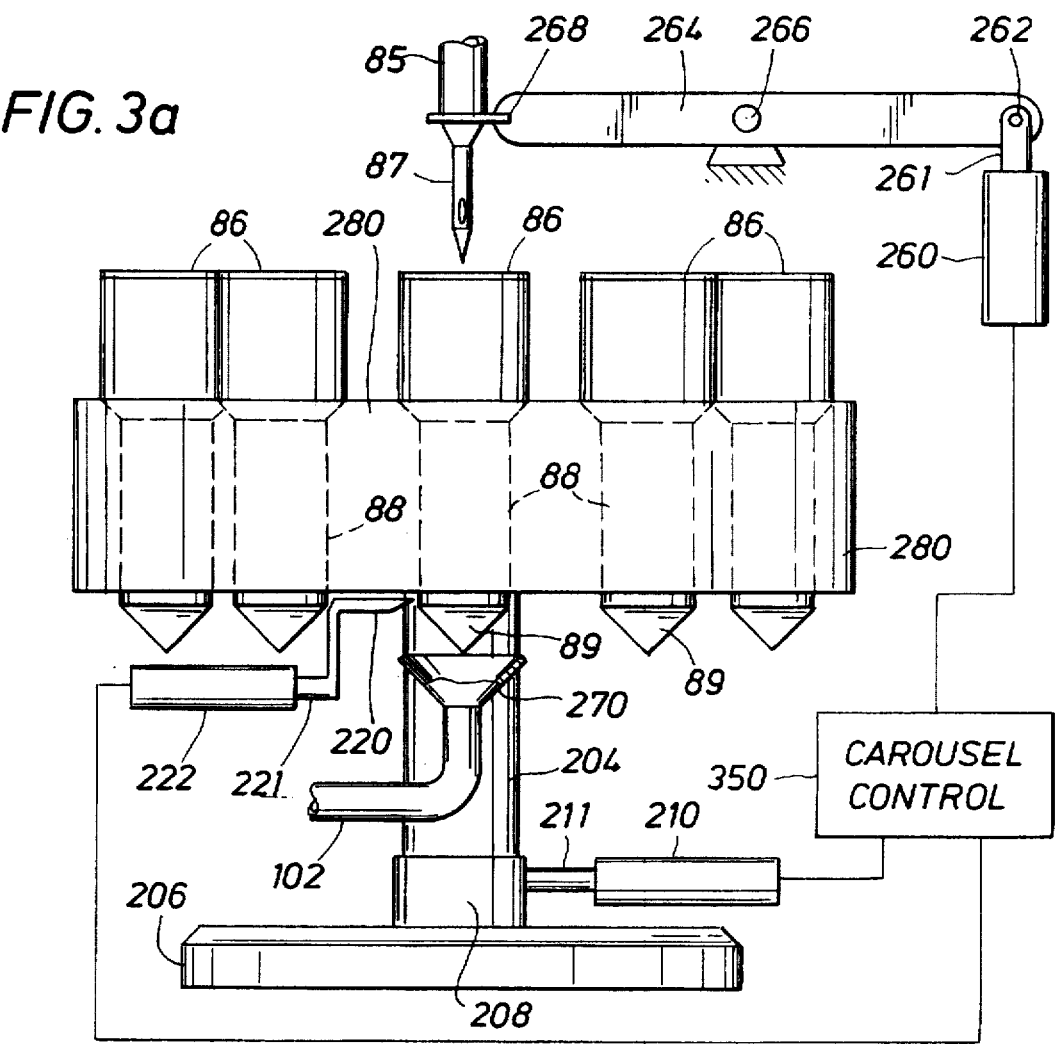

METHOD AND APPARATUS FOR GATHERING AND PREPARING LIQUID SAMPLES FOR ANALYSIS

BACKGROUND OF THE INVENTION

1. Field of the Invention

This invention is directed toward apparatus and methods for gathering and preparing liquid samples for analysis, and more specifically directed toward the gathering and preparing of water samples for analysis for tritium content, where the samples are collected from underground formations penetrated by a borehole or collected at varying depths in surface canals and the like.

2. Background of the Art

The monitoring of liquid samples for contaminants is quite common in today's industrialized society. Such monitoring is carried out to track the efficiency of various manufacturing processes. In addition, such monitoring is employed to monitor potential hazards to humans and to the environment resulting from various manufacturing and processing operations.

Many types of nuclear manufacturing and processing facilities were built in significant numbers starting in the late 1940's and early 1950's. In the following decades, even more such facilities were built world wide as a result of the proliferation nuclear power, nuclear weaponry, and nuclear medicine. As with most manufacturing and processing operations, nuclear facilities generate wastes which can be hazardous to the environment and to the human and animal population, and such wastes must be monitored and disposed using methods which minimize health and environmental risks.

Attention is now directed toward nuclear facilities designed for the manufacture of nuclear weapons. More particularly, attention is directed toward "fission" weapon facilities used to produced weapons based upon induced neutron "chain" reactions in certain isotopes of uranium and plutonium. Great quantities of energy are released as a result of the induced chain reaction which is often referred to as an "atomic explosion". It is well known that one precursor for such an energy release or explosion is a "critical mass" of the fission material in order to sustain the chain reaction. Weapons designers also found in the 1940's that more efficient energy releases or explosion could be obtained if the chain reaction were initiated with a burst of neutrons from a device known in the art as a "trigger".

Several techniques have been used in nuclear weapons to construct triggers which produce large neutron fluxes for relatively short periods of time. The most common trigger is based upon the reaction

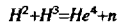

where $H^2$=deuterium which is a hydrogen atom with a nucleus containing a neutron as well as a proton;

$H^3$=tritium which is a hydrogen atom with a nucleus containing two neutrons as well as a proton;

$He^4$=helium; and n=a neutron.

That is, when tritium is bombarded with deuterium at a sufficient energy, a nuclear reaction occurs which yields helium, plus a neutron with approximately 14 million electron volts (MeV) of energy. Triggers based upon this "deuterium-tritium" reaction therefore produce the neutron flux desired as a trigger for fission type weapons.

Tritium is used at fission type weapons manufacturing facilities and, as might be expected, most of these manufacturing facilities produce significant amounts of tritium. Tritium is radioactive with a half life of approximately 12.33 years, and decays to ground state $He^3$ by the emission of a beta particle. Tritium reacts chemically as "normal" hydrogen ($H^1$). It is well known that hydrogen is easily ingested by plant life and animal life including humans. Tritium is likewise easily ingested, but tritium ingestion results in the possible chemical binding of radioactive tritium within the plant or animal organism. As an example, tritium ingested by a human would result in radioactive tritium atoms being chemically bound or "lodged" within the human. Subsequently, as the tritium decays with a half life of 12.33 year, beta particles are emitted at the sites of the bound tritium causing significant biological and cellular damage in the area of emission. It is apparent, therefore, that waste liquid, such as water which is contaminated with tritium, can be a significant health threat to humans and to the environment. Such tritium contaminated water can be found in cooling ponds and drainage canals in the vicinity of nuclear facilities such as nuclear weapons plants. Furthermore, run-off water, which migrates and percolates into the earth around nuclear facilities, can also be contaminated with tritium. This becomes an especially critical problem if these contaminated waters migrate into drinking water aquifers. The result is a potable aquifer contaminated with a beta emitting tritium with a half life of 12.33 years.

Nuclear sites are currently monitored for tritium wastes. Liquid samples such as water are collected at varying depths from cooling ponds or canals. To monitor the migration of tritium contaminated water toward the water tables, test wells are often drilled about the site, ground water is allowed to flow into each of these wells, and water samples are taken at varying depths within the well. As an example, the detection of tritium contamination in a water sample gathered near the surface usually indicates that contaminated water has not migrated to deeper aquifers. Furthermore, the combination of tritium concentration measurements made at multiple depths in multiple wells can be used to generate a three dimensional map of any tritium contamination in the ground beneath the nuclear facility. Since nuclear facilities can be quite large and cover hundreds if not thousands of acres, it should be understood that tens or even hundreds of monitor wells are required to properly monitor water movement and possible ground water contamination.

Again examining current tritium monitoring techniques, liquid samples gathered from monitor wells, or at different depths within surface ponds or canals, must be pretreated prior to analysis for tritium. In one such pretreatment, the water is passed through a column containing a plurality of resin materials in order to remove certain cations and other materials which prohibit accurate tritium concentration measurements. This pretreatment can be performed at the sample site, but, using current technology, is preferably performed at a remote, analytical laboratory under controlled conditions. Tritium analysis is currently being performed at the remote, analytical laboratory. The time required to perform this type of analysis often takes one to two months from the time samples are received. The analysis cost per sample is also quite high. Considering that multiple sample sites such as monitor wells are needed, and that samples should be taken at varying depths at each sample site, the total cost of a monitor survey can be quite high. Furthermore, it is highly desirable to sample at a given site, such as a monitor well, as many as three to four times per day in order to detect early any tritium contamination so that remedial actions can be taken immediately. Although sampling at this time frequency can be done today, the current sample analysis turnaround of one to two months negated the usefulness of this method.

One object of the present invention is to provide apparatus and methods for efficiently obtaining liquid samples at multiple sample sites and at multiple depths at each site. This is accomplished by a novel submersible pump system which can quickly be filled and which can quickly transfer sample to the surface from varying depth within the liquid.

Another object of the present invention is to provide apparatus and methods for efficiently treating, at the sample site, the samples obtained at varying locations and varying depths. This is accomplished by a valving system cooperating with a controller system such that the required sample is obtained, treated, and provided to an analyzing system upon command.

A further object of the invention is to provide apparatus and methods so that each sample site can be sampled at varying depth three to four time per day, and that these samples can be pretreated prior to analysis.

Still another object of the present invention is to provide apparatus and methods for pretreating and analyzing a sample such that the concentration of tritium within the sample can be obtained, at the sample site, within thirty minutes after initiation of the pretreating and analysis steps.

A additional object of the invention is to provide apparatus and methods for gathering, pretreating, and analyzing water samples for tritium content completely under the control of a microprocessor controller and timer, and without human intervention.

There are other objects and applications of the present invention which will become apparent in the following disclosure.

SUMMARY OF THE INVENTION

The invention is directed toward apparatus and methods for gathering and preparing liquid samples for analysis for elements or compounds within the liquid samples. Although applicable to a variety of liquids and to a variety of elements or compounds, the preferred embodiment of the invention is directed toward the gathering and pretreating of water samples for tritium analysis. This disclosure is further directed toward apparatus and methods for the gathering or collecting of water samples from underground formations penetrated by a borehole, or collecting water samples at varying depths in surface canals, ponds, and the like. The invention is particularly suited for monitoring water in the vicinity of nuclear manufacturing, fabrication and disposal facilities for tritium contamination of ground waters.

The sampling system includes submersible pumps and a vacuum/compressor system and valving system for operating these pumps in order to gather liquid samples at varying depth below the surface of the earth, and transporting these samples to the surface of the earth for pretreatment prior to analysis for contaminants. For purposes of discussion, it will be assumed that the liquid is water and that the contaminant is tritium.

Although the system can be used to sample only one location, one of its main advantages is that multiple locations can be sequentially sampled or "monitored" for tritium contamination. As mentioned previously, the system can be used to obtain samples from below the surface, such as water samples from subterranean wells, from cooling ponds, canals and the like. Again, for purposes of discussion, it will be assumed that the water samples are being obtained at varying depths in a plurality of well boreholes. Each well is preferably lined or "cased" with a steel, plastic or composite liner to prevent the respective boreholes from caving in. A submersible pump is positioned within each well, and water samples from each well are taken by the submersible pumps sequentially and automatically under the control of a microprocessor and timer. The valving system of each submersible pump includes a spring loaded check valve which can be set to operate at above a certain hydraulic pressure. This, in turn, allows a given pump to obtain a water sample only below a given depth corresponding to the selected hydrostatic pressure. This feature allows sampling at varying, pre selected depths as will be discussed in detain is a subsequent section of this disclosure.

Samples from each pump, therefore each well, are transferred or "evacuated" to the surface for pretreating and analysis. The compressor/vacuum pump system cooperating with a valving system, which also includes flow lines, is used to transfer the samples to the surface. Specifics of the operation of the valving system will subsequently be presented in detail. At this point, it suffices to say that the vacuum/compressor system and the valving system, under the control of the microprocessor and timer, are used to control the flow of the sample water. Furthermore, these systems are also used to flow purge air and wash water within the sample in order to clean the system between sampling sequences so that the next sample will not be contaminated by the previous sample.

The valving system cooperates with a carousel mechanism which holds a plurality of columns in which sample water is pretreated prior to analysis for tritium. The term "pretreated" is used to delineate this step of the analysis from any "treatment" of the sample that might be required in the analysis of the sample within a tritium analyzer. The carousel mechanism is operated mechanically by cylinder and piston devices powered by the compressor/vacuum pump system under the control of a carousel controller which, in turn, is under control of the system microprocessor and timer. This feature of the invention greatly increases the speed and automation of the pretreatment phase of the sampling and analysis process.

Once each collected water sample has been treated in a specific sample pretreatment column held by the carousel mechanism, the sample is then passed to an analyzer for analysis by means of the valving system and its accompanying flow lines. This transfer is also under control of the system microprocessor and timer, which cooperates with the analyzer by means of communication signals. Tritium concentration is preferably measured with a chromatographic analyzer such as a Radiomatic HPLC high precision liquid chromatographic unit. Results of each sample analysis are displayed with an appropriate analog or digital meter, printed by means of a printer, or recorded on a magnetic disk or other digital recording device.

All of the previously discussed elements of the system, with the exception of the submersible pumps and some elements of the valving system and flow lines, are preferably located at the surface of the earth.

The plurality of submersible pumps used in the invention rapidly and automatically obtain samples and transfer these samples to the surface for pretreatment and analysis. The pumps are also automatically purged after sample transfer such that the next sample will not be contaminated by the previous sample.

The invention also provides rapid and automatic means for pretreating each sample prior to analysis by using the carousel mechanism in cooperation with the valving system and the system microprocessor and timer. This means increases the accuracy and precision of the overall analysis method, while reducing cost by eliminating the need for manual sample pretreatment. Furthermore, the samples can be pretreated on site thereby reducing the overall sampling and analysis time when compared with current methods.

The valving system of the submersible pumps is such that each sample site can be sampled at varying depth. Furthermore, the system microprocessor and timer can be programmed so that multiple samples are obtained sequentially in time from the same well at the same depth. Since the entire sampling and pretreatment system is fast, efficient and automatic, each well can be sampled and analyzed at the same depth as often as three to four time per day. This makes the system ideally suited for monitoring tritium at facilities where contamination can be sudden. As an example, using a four time per day sampling, the maximum time interval between samples is six hour. Since sample pretreating and analysis is done on site in approximately thirty minutes, the maximum time that can elapse after contamination such as a spill is slightly more than six hours. This rapid detection capability of the invention permits rapid remedial action to be taken, especially when compared with typical one to two month sample analysis turnaround times of present, off site, commercial tritium analysis services.

In summary, the sequence of sample acquisition and sample pretreatment events, described briefly above, are controlled by the system microprocessor and timer thereby eliminating need for direct human operation. This substantially reduces the cost and increases the accuracy of sampling and pretreating compared to present human operated systems. The entire sampling, pretreatment and analysis sequence requires less than thirty minutes thereby analysis results to be obtained very rapidly when compared with present, commercial, off site tritium analysis services. The entire sampling and pretreatment system is relatively small and portable, as is the preferred analyzer. Sample analysis can therefore be obtained on site within thirty minutes compared with the typical one to two month turn-around of present, commercial, off site analysis services.

BRIEF DESCRIPTION OF THE DRAWINGS

So that the manner in which the above recited features, advantages and objects of the present invention are attained and can be understood in detail, more particular description of the invention, briefly summarized above, may be had by reference to embodiments thereof which are illustrated in the appended drawings.

FIG. 2 illustrates the major elements of a sample pretreatment column;

FIG. 3a is a side view of the carousel mechanism;

FIG. 3b is an abbreviated top view of the carousel mechanism; and

DETAILED DESCRIPTION OF THE PREFERRED EMBODIMENTS

3. Overview of the System

Figure 1:
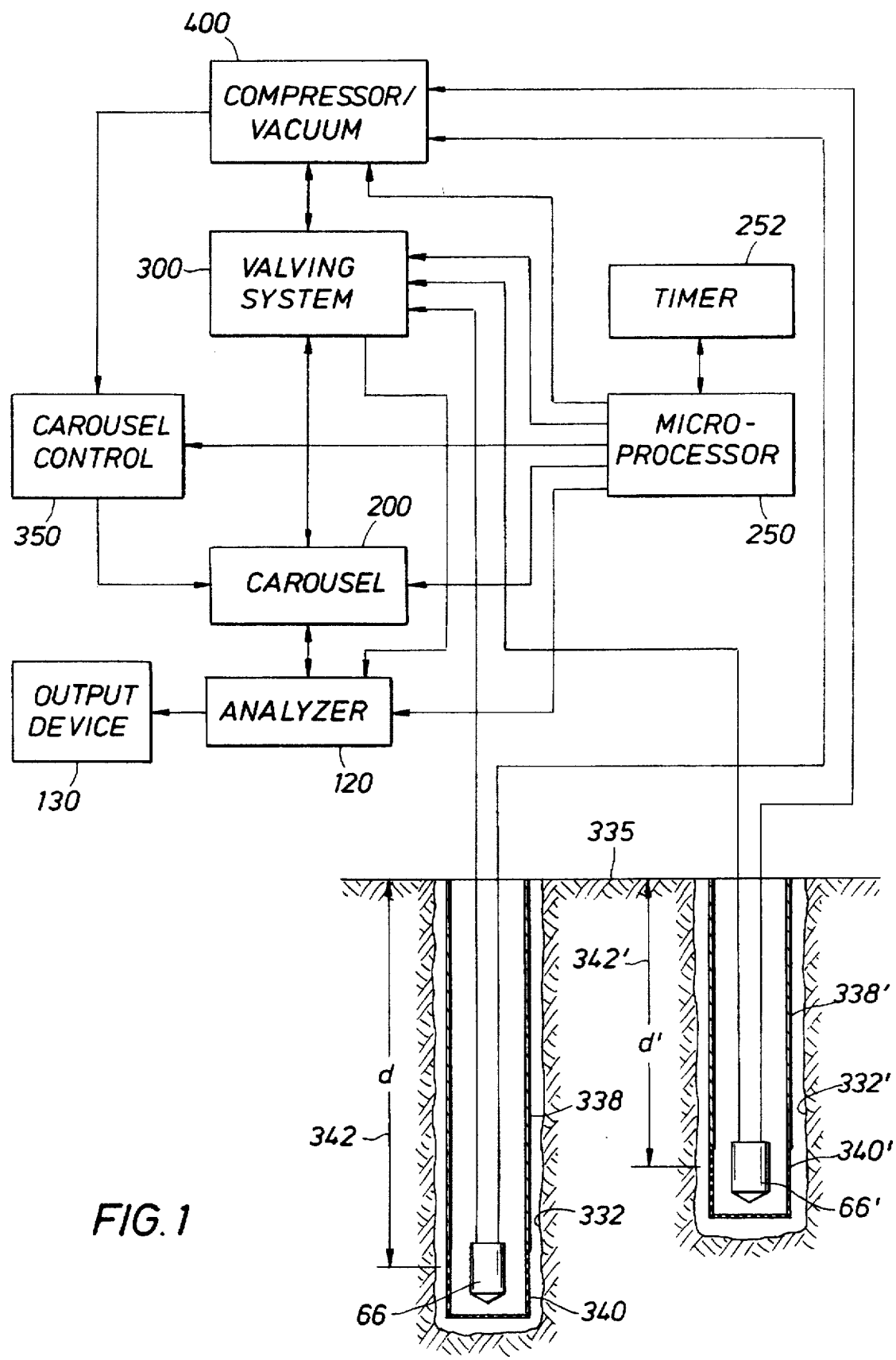
FIG. 1 is a functional block diagram of the sampling and pretreatment system, and illustrates how this system cooperates with an analyzer.

FIG. 1 represents a functional diagram of the sampling and pretreating system which cooperates with a tritium analyzer.

The system is depicted in FIG. 1 as gathering samples from two wells 332 and 332'. Each well is preferably lined or "cased" with a steel, plastic or composite liner 338 and 338' to prevent the respective boreholes from caving in. Near the bottom of the casings 338 and 338', perforated screens 340 and 340' are affixed to aid the flow of water from the surrounding ground formations into the boreholes of the respective monitor wells. Monitor wells are of preferably differing depths d and d', where these dimensions are denoted by the numerals 342 and 342', respectively. A submersible pump 66 is positioned within the well 332 in the region of the liner 66. Likewise, a submersible pump 66' is positioned within the well 332' in the vicinity of the screen 340'. It should be understood that the invention is not limited to monitoring two wells, but can be used to monitor only one well, or a plurality of wells greater than two. Furthermore, the invention is not limited to monitoring water which flows into well boreholes, but can also be used to monitor water in cooling ponds, canals, lakes and the like.

Still referring to FIG. 1, each pump 66 and 66' cooperates with a compressor/vacuum pump system 400 which is used to fill the pumps with liquid sample, and then to transfer these samples to the surface for pretreating and analysis. The compressor/vacuum pump system cooperates with a valving system, which also includes flow lines, denoted by the block 300. Specifics of the operation of the valving system 300 will subsequently presented in detail. At this point in the disclosure, it suffices to say that the valving system 300 is used to control the flow of the sample liquid, and the flow of purge air and wash water for the system.

Still referring to FIG. 1, the valving system cooperates with a carousel mechanism 200 which holds a plurality of columns in which sample water is pretreated prior to analysis. The carousel mechanism is operated mechanically by cylinders and piston devices powered by the compressor vacuum pump system 400 under the control of a carousel controller 350.

Once each collected water sample has been treated in a specific column carried by the carousel mechanism 200, the sample is then passed to an analyzer 120 for analysis by means of the valving system 300 and its accompanying flow lines. If the sampled liquid is water and the contaminant to be measured is tritium, a chromatographic analyzer such as a Radiomatic HPLC high precision liquid chromatographic unit manufactured by Hewlett Packard can be used as the analyzer 120. Results are displayed with an appropriate output device 130 such as a analog or digital meter, printed by means of a printer, or recorded on a magnetic disk or other digital recording device.

Again referring to FIG. 1, all of the previously discussed elements of the system, with the exception of the submersible pumps 66 and 66' and some elements of the valving system and flow lines, are preferably located at the surface of the earth 335. Furthermore, the compressor/vacuum system 400, the valving system 300, the carousel 200 and the carousel controller 350 are preferably controlled by a microprocessor 250 and a timer 252. Stated another way, the sequence of events described briefly above and described in detail in subsequent sections, are preferably implemented by a programmed microprocessor 250 and timer 252. The timing of the analyzer 120 is preferably independent of the microprocessor 250 and timer 252. The microprocessor 250 does, however, send signals to the analyzer 120 at a point in time when each gathered sample has been pretreated and is ready for acceptance by the analyzer 120 for analysis for contaminants such as tritium.

4. Pretreatment Sample Column

FIG. 2 illustrates a sample pretreatment column identified by the numeral 88. The column is filled with a plurality of resins, illustrated conceptually and identified with the numeral 88', which are selected and designed to remove certain cations and other contaminants from the water sample which would tend to introduce error in the subsequent tritium concentration when the pretreated sample is passed to the tritium analyzer 120 (see FIG. 1). Each column is sealed at an upper end 86 and a lower end 89 to prevent contamination of the resins prior to pretreating sample. Referring to both FIG. 1 and FIG. 2, one sample pretreatment column in mounted within the carousel 200 for each sample acquired and analyzed. Sample from the submersible pump 66 within the well being sampled is passed through a valving system and through the flow line 85 and through a hollow needle 87 which penetrates the upper end 86 of the column housing 88 by mechanical actions described in a subsequent section. Sample fluid is pumped through the column 88 and out through the lower end 89 after it has been removed or "broken" by mechanical actions likewise described in a subsequent section. The pumping of sample liquid through the column 86 constitutes the pretreatment of the sample prior to analysis for tritium. Sample pretreatment columns suitable for this purpose are manufactured by the Iomega Corporation.

5. The Carousel Mechanism

A side view of the carousel mechanism is shown in FIG. 3a. A tray 280 holds a plurality of sample pretreatment columns 88. The preferably circular tray 280 can rotate about a support column 204 which is affixed to a support base 206. One arrangement for the sample pretreatment columns 88 in the tray 280, and the position of the support column 204, is better shown in the abbreviated top view of the carousel mechanism shown in FIG. 3b.

Referring again to FIGS. 3a and 3b, the tray 280 is rotated such that each sample pretreatment column 88 is sequentially positioned immediately below a hollow needle 87 and immediately above a functionally illustrated flow receptacle 270 which is connected to a flow line 102. The tray 280 is rotated by a ratchet assembly 208 which cooperated with a pneumatic piston 211 and cylinder 212. Compressed air is supplied to the piston/cylinder assembly through the carousel controller 350 which cooperates with the compressor/vacuum system 400.

Once a sample pretreatment column 88 is in place, it is necessary to pump sample water through the column in order to obtain the desired pretreatment of the sample. Recalling that each column is sealed to avoid contamination before use, it is necessary to establish a fluid flow path through the properly positioned column 88. The upper end 86 of the column is penetrated by moving the hollow needle 87 downward by the activation of a pneumatic piston 261 and cylinder 260. Again, compressed air is supplied to this piston/cylinder assembly through the carousel controller which cooperates with the compressor/vacuum system 400. The piston is attached to a lever 264 at a pivot 262 by means of a swivel. The lever pivots about a fixed point 266, and the left end of the lever is attached by means of a swivel to a bracket 268 affixed to the hollow needle 87. When activated, the piston 261 moves upward thereby driving the hollow needle 87 through the top 86 of the column 88.

The bottom tip 89 of the column is sheared or broken by the action of a cutter 220 which is attached to a pneumatic piston 221 cooperating with the pneumatic cylinder 222. Once again, compressed air is supplied to the piston/cylinder assembly through the carousel controller 350 which cooperates with the compressor/vacuum system 400. When activated, the piston 221 and attached cutter 220 moves to the right thereby breaking the tip 89 of the column 88 and establishing a flow path through the column and resins 88' contained within. Fluid leaving the column is collected by a flow receptacle which is shown functionally as the element 270. Pretreated sample then flows through a flow line 102 to the analyzer 120. The tray 280 is then rotated such that the next column is positioned for sample flow through. It is emphasized the mechanisms used to rotate the tray 280, to penetrate the top 86 of the column 88, and to break the lower tip 89 of the column 88 are functional illustrations for brevity and clarity, and that other pneumatically powered mechanical arrangements and devices are equally suited to perform these tasks.

6. Sample, Pretreatment and Analysis Sequence

Figure 4:
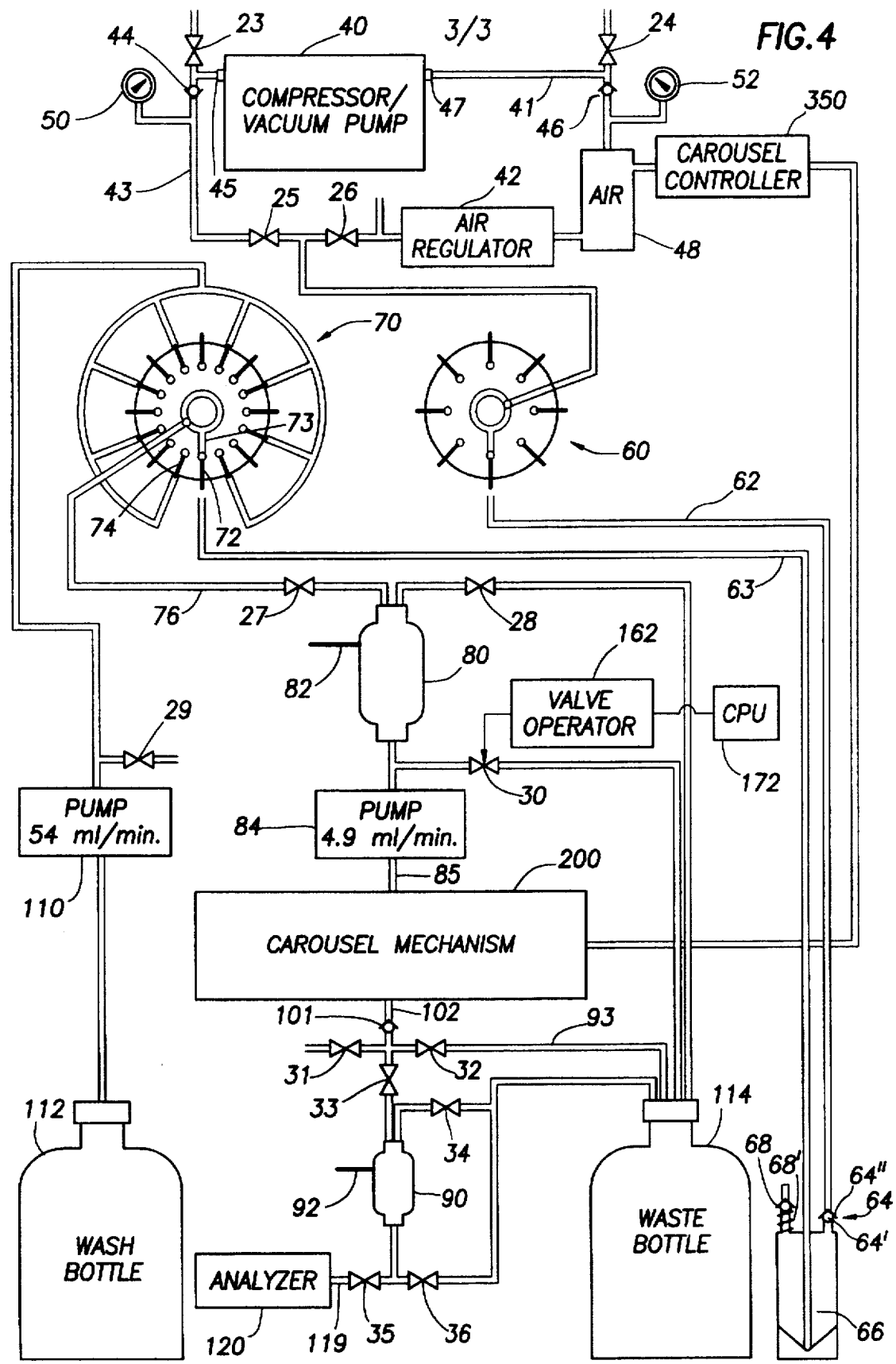
FIG. 4 is a more detailed illustration of the sampling and pretreatment system cooperating with an analyzer.

An illustration of the sampling sequence for a given well will now be disclosed in detail. FIG. 4 illustrates the sampling system in more detail, and will be used heavily in the coming discussion. FIG. 1, however, shows the system microprocessor 250 and timer 252 (see FIG. 1) in order to enhance the clarity of FIG. 4. It should be understood, however, that system elements are timely operated by the timer and microprocessor as specified in previous and subsequent discussion.

In detailing the operation of the apparatus, it will be assumed that eight wells are to be monitored, and that a well designated as well No. 5 is currently being sampled. The system is configured to sample eight wells, and is illustrated while in the process of sampling well No. 5, as shown in FIG. 4. Wells No. 1 through 4 have been sampled, and wells No. 6–8 remain to be sampled in the illustrated sample sequence. It should be understood, however, that the apparatus can be tailored to monitor fewer than eight wells or more than eight wells. It should also be understood that cooling ponds or canals, rather than wells, can likewise be monitored, and that wells, ponds, canals, building basements and the like can be monitored at varying depths as will be discussed further in a subsequent section of this disclosure

A. Initiation of the Sequence for a Given Well

Referring to FIG. 4, a pump 40 of the compressor/vacuum system 400 serves as both a compressor and a vacuum pump in the operation of the system. Upon start-up of the sampling and pretreating procedure, the pump 40 is activated and a valve 24, which vents the compressor line 41 of the pump 40, is in the closed position. Air is drawn into the pump 40 through a vent valve 23, which is in the open position, and into a vacuum side 45 of the pump 40. Air compressed by the action of the pump 40 flows out through a compression side 47 and into an air tank 48 by means of line 41. A check valve 46 prevents air flowing from the air tank 48 back toward the pump 40. Pressure within the air tank 48, which is indicated by a gauge 52, is allowed to reach approximately 100 psi. As was explained in detail in a previous section, compressed air within the air tank 48 is used to rotate the carousel mechanism 200 used to transport the pretreatment sample columns, to penetrate the tops of these columns to receive sample liquid, and to remove the bottoms of these columns to allow sample to flow eventually to the sample analyzer 120 to be analyzed for tritium concentration. Compressed air is also used to transfer samples collected by the submersible pump 66 to the surface of the earth.

B. Filling the Submersible Pump

Again referring to FIG. 4, a vacuum is applied to the submersible pump 66 (in a specified well) by means of the line 62. Valve 23 on the vacuum side 45 of pump 40 is closed. Valve 25 is opened, and valve 26 is closed thereby applying a vacuum, which is monitored with a gauge 50, to an eight position rotary valve 60 of the type manufactured by Valco Instruments, Inc. of Houston, Tex. The vent valve 24 on the compressor side 47 of the pump 40 is opened. Recalling that the sampling of well No. 5 is being used as an example, the valve 60 is positioned to transfer the applied vacuum through line 62 to a hydro check valve 64 mounted on the pump 66. Liquid from the well bore (see FIG. 1) then flows into the submerged pump 66 through the check valve 68. When the water level within the pump reaches the ball 64' of the hydro check valve 64, it floats and is then pressed against the seat 64" thereby isolating the pump from the vacuum in line 62. The check valve 68 is spring loaded by a spring 68' to open only above a predetermined hydrostatic pressure. This "cracking" pressure must be greater than the head pressure seen by the pump 66 when placed at a given depth. This controls or prevents sample liquid from flowing into the pump until a vacuum is applied at the valve 64. Valves that are available commercially and that are suitable for use as the valve 68 are available in four cracking pressures which are ½, 1, 10, and 25 pounds per square inch gauge (psig). The following chart shows the maximum depth that the pump can be immersed in water for each different cracking pressure for the valve 68.

| Cracking Press. (psig) | Max. Depth (feet) |
|---|---|
| ½ | ½ |
| 1 | 2 |
| 10 | 20 |
| 25 | 50 |

C. Evacuating the Submersible Pump

Still referring to FIG. 4, once the pump 66 is filled with sample liquid, it is necessary to retrieve the sample at the surface of the earth by evacuating the pump. Valve 25 is closed to isolate the pump 66 from the vacuum side 45 of the pump 40. Valve 23 is opened and valve 24 is closed thereby supplying compressed air to the valve 60 through the open valve 26 from the air tank 48 and a n air regulator 42. The pressure within the air tank 48 in monitored with a gauge 52. The air regulator 42 is preferably adjusted so that the pressure at the open valve 26, and correspondingly at the output connected to well No. 5 from the valve 60, is approximately 25 pounds per square inch (psi). Compressed air is then transferred through line 62, through the hydro check valve 64, and into the interior of the pump 66. This displaces sample fluid within the pump 66 upward through a line 63 to a sample intake port of a sixteen position valve 70 of the type manufactured by Valco Instruments, Inc. of Houston, Tex. The captured sample liquid is thereby transferred from the downhole pump 66 to the surface of the earth for evaluation.

D. Filling Reservoir Prior to Pretreatment

Sample fluid is displaced from the pump 66 and flows through the valve 70. Again referring to FIG. 1, valve 27 is open and valve 28 is closed so that sample fluid flows out of the valve 70 through the flow line 76 into a reservoir 80. The preferred volume of sample deposited into the reservoir 80 is approximately 50 cubic centimeters (cc), and this volume is verified by a capacitive proximity switch 82. Once the chamber 80 is filled with sample liquid as sensed by the switch 82, the valve 27 is closed while the valve 28 remains open. The sample liquid within the reservoir 80 is now ready to be pretreated.

E. Pretreating the Sample and Transfer to the Analyzer

A sample pretreatment column 88 is positioned by the carousel mechanism 200, as described previously, for sample pretreatment. Referring now to FIGS. 4 and 3a, the desired column positioning is obtained by rotating the carousel tray 280 by the activation of the pneumatic cylinder 210 and cooperating piston 211. The top 86 of the positioned column 88 is penetrated by the hollow needle 87 by activating the pneumatic cylinder 260 and cooperating piston 261. The bottom tip 89 of the positioned column 88 is broken by the activation of the pneumatic piston 221 and cooperating cylinder 222. Compressed air to activate these pneumatic devices is supplied from the air tank 48 under control of the carousel controller 350.

Still referring to FIGS. 4 and 3a, sample fluid is now able to be pumped by a pump 84 from the reservoir 80 through a flow line 85, through the hollow needle 87, through the resins 88' contained within the column 88, out the bottom of the column 88, through the flow receptacle 270, through the flow line 102 and through the check valve 101. The pump 84 operates preferably at a rate of 4.9 milliliters per minute (ml/in). Valve 32 is opened and valves 31 and 33 are closed so the approximately 10 cc of the 50 cc of sample contained in the reservoir 80 is pumped through a flow line 93 into a waste bottle 114. This purges the valve 101 of any contaminants from the previous sample. This requires approximately two minutes. Valve 31 is then opened briefly to purge the flow line 93 of any liquid by using dry air from a purge gas source (not shown). This purge flows to the waste bottle 114.

Referring to FIGS. 1, 3a and 4, valves 31 and 32 are then closed and valves 33 and 34 are opened. Approximately 10 ml of sample fluid are then pumped by the pump 84 into a sample holder 90, with the 10 ml volume being confirmed by the capacitive proximity switch 92. When the sample holder is filled with the desired 10 ml of sample fluid, the valve 33 is closed and valve 34 remains open. A signal is then sent to the system microprocessor 250 indicating that the sample container 90 holds a sample which has been pretreated and which is now ready to be analyzed for tritium content by the analyzer 120. Furthermore, a communication channel signifies that the sample is from a given source, which in the example being discussed is well No. 5. Valve 35 is then opened and the sample stored in the sample chamber 90 is flowed through the valve 35 and through the flow line 119 to the analyzer 120 for analysis.

F. Purging of the System

After each sample acquisition, pretreatment and analysis, the system must be purged so that the next sample will not be contaminated by remnants of the previous sample.

Referring to FIG. 4, the valves 27, 28 and 29 are opened and purge gas, preferably dry air from a purge gas source (not shown), is introduced through opened valve 29. This effectively clears the sample position conduit 72 of the valve 70 for the well being sampled (well No. 5 in this example), the flow line 76, the sample chamber 80, and other connecting lines shown in FIG. 4. The purge gas and any remaining liquid sample is driven to the waste bottle 114. The valves 32, 33, 34, and 36 are then opened, the valve 35 is closed, and purge air is introduced through the open valve 31 thereby purging remnant liquid sample from flow line 93 and from the sample chamber 90 into the waste bottle 114.

Next, appropriate elements of the system are washed (with preferably de-ionized water) to further remove traces of the prior sample in order to avoid contaminating the next sample. Still referring to FIG. 4, the valves 29, 30, 33 and 31 are then closed, and the valve 32 is opened. The sixteen position valve 70 is then rotated, by the pneumatic system previously described, one position (counter clockwise as shown in FIG. 4) so that the wash conduit 74 for well No. 5 is aligned with the main flow conduit 73. Next, preferably de-ionized water is pumped from a wash bottle reservoir 112 by means of a pump 110 through the valve 70, the flow line 76, the chamber 80, the pump 84, the column 88, and the flow line 93 into the waste bottle 114. The pump 110 operates at preferably 64 ml/min. With the above valve settings, approximately 20 cc of de-ionized water are pumped to flush the chamber 80 and the column 88. Next, valves 32, 36 and 31 are closed, valves 33, 34, and 36 are opened, and the de-ionized water is pumped through the sample bottle 90 and adjacent flow lines and deposited into the waste bottle 114. Finally, purge gas, preferably again from the source (not shown) of dry air, is flowed through all elements washed with de-ionized water by sequentially opening the appropriate valves as depicted in FIG. 4.

After completing the sample gathering, pretreating, sample analysis and system purge operations, the carousel tray 280 is rotated, using previously described apparatus and methods, such that a fresh column 88 is positioned for the treatment of the next sample. Likewise, the valves 60 and 70 are positioned for the next sample, which will be a sample from well No. 6 in the example being discussed.

The system microprocessor 250 in FIG. 1 is provided with a central processing unit (CPU) and sequentially controlled instructions in a memory. The system of FIG. 4 shows a number of binary (meaning two position) valves which are all provided with valve operators, and the preferred form is a solenoid valve operator. A single valve 30 is shown in FIG. 4 with a valve operator 162 for timed operation. The valve operator 162 is controlled by the CPU, identified by the numeral 172, which is an element of the system microprocessor 250 shown in FIG. 1. All other binary valves shown in FIG. 4 are operated in the same manner, however specific functional relationships (as shown for valve 30) have been omitted from FIG. 4 for clarity. In a like fashion, the valves 60 and 70 are driven by incremental rotary operators, one choice being supplied by the valve maker. They ratchet (or rotate) by increments to index by positioning the valves 60 and 70 to the next position.

While the foregoing disclosure is directed toward preferred embodiments, the scope of the invention is set forth by the claims which follow.

I claim:

1. A method of inspecting for heavy water in the vicinity of a nuclear facility comprising the steps of:
    (a) forming a water well to draw water into the water well from underground water bearing strata in the vicinity of a nuclear facility;
    (b) periodically removing with a pump means a measured sample of water from one or more specified depths in said water well, wherein said pump means receives said sample when hydrostatic pressure to which said pump means is exposed exceeds a predetermined value;
    (c) sizing the sample so that each sample is sized to a selected size; and
    (d) removing the samples to a test site to undergo testing.
2. The method of claim 1 wherein at least two wells are drilled in the immediate vicinity of the nuclear facility and the samples obtained therefrom are removed from the wells by pumping with said pump means from a specified depth in the respective wells, and collecting the samples in individual dedicated sample receiving storage containers.
3. The method of claim 2 wherein said well water samples are collected from different water bearing strata.
4. The method of claim 1 wherein said pump means comprising a water pump is installed in the well, and subsequently including the step of
    controllably operating the pump by a first fluid line connecting to the pump from the surface to initiate pump operation, and
    recovering said sample from the well by pumping water from said specified depth through the pump and through a second fluid line connecting from the pump.
5. The method of claim 1 including the step of collecting samples from multiple wells near the nuclear facility where:
    (a) each well is individually pumped with said pump means to recover individually, at a specified depths a sample from the particular well;
    (b) each said sample is isolated from other collected samples; and
    (c) all the samples are collected in a uniquely identified timed sequence with respect to each said specified depth in each said well.
6. An apparatus for recovery of heavy water samples at a nuclear facility comprising:
    (a) a sample delivery pump adapted to be located at a specified location provided with artesian water near the nuclear facility;
    (b) a multiple position, controlled valve system having plural similar output connections wherein a designated output connection of said similar output connections is fluidly connected by said valve system to said pump, and said connection is adopted for periodic interruption;
    (c) means connecting said valve system with said pump with two lines thereto wherein a first line enables provision of a pumping signal to said pump to receive a water sample, and the second line enables said pump to deliver said water sample from said pump;
    (d) a sample storage container having upper and lower sample container closure members to provide a closed sample container; and
    (e) a controller operating said valve system and said pump so that a fresh sample is periodically recovered from said pump through said valve system and into a clean sample container.
7. The apparatus of claim 6 wherein said pump is detachable to enable positioning in a sample collecting location and said pump comprises:
    (a) an inlet to receive water sample through a differential pressure valve thereby initiating collection of water sample by said pump;
    (b) an outlet to deliver collected sample; and
    (c) a pump housing supporting said inlet and said outlet.
8. The apparatus of claim 7 further including:
    (a) a surface located pump fluid power source to provide fluid at a differential pressure to operate said pump; and
    (b) a switch to control operation of said power source.
9. The apparatus of claim 8 including a rotatable carousel to support a set of said sample containers to receive a set of samples.
10. The apparatus of claim 9 including a pre-processing reagent in each of said sample containers, and also including a needle connected to an inlet line wherein said needle and each said sample container is positioned such that fresh sample is flowed through said inlet line and into said sample container through said needle.

11. The apparatus of claim 10 wherein:

(a) each sample is pretreated with said pre-processing reagent; and (b) each pretreated sample is transferred to a tritium analyzer wherein said sample is analyzed for tritium content.

12. The apparatus of claim 11 wherein:

(a) a plurality of said pretreated samples are transferred to said tritium analyzer for analysis; and (b) said tritium analyzer is purged between each said analysis.

13. The apparatus of claim 6 wherein said valve system comprises:

(a) a first rotary valve which is connected to said pump by said first line;

(b) a second rotary valve which is connected to said pump said second line;

(c) wherein the operation of said first and second rotary valves is controlled by said controller to operate said pump and to transfer said water sample from said pump into said sample container.

14. A method of inspecting for heavy water in the vicinity of a nuclear facility comprising the steps of:

(a) forming multiple water wells to draw water into each water well from underground water bearing strata in the vicinity of a nuclear facility;

(b) periodically removing a measured sample of water from one or more said water wells at specified depths in said water well;

(c) sizing the sample so that each sample is sized to a selected size; and (d) removing the samples to a test site to undergo testing, wherein (i) each well is pumped individually to recover individually, at a specified depth, a sample from the particular well, (ii) each said sample is isolated from other collected samples, (iii) all the samples are collected in a uniquely identified timed sequence with respect to each said specified depth in each said well, (iv) the samples are temporarily stored in sample containers which are mounted on a motorized sample container alignment means, and (v) said samples are subsequently removed from said sample container to test for heavy water.

15. The method of claim 14 wherein said sample containers are aligned by said alignment means for periodic and sequential opening to receive said samples.

16. The method of claim 15 including the additional steps of:

(a) forming a closed storage container for a measured quantity of water;

(b) transferring each said sample in timed sequence to said storage container, and (c) then opening the closed storage container to remove said sample.

17. The method of claim 16 including the step of removing water from said storage container to a heavy water analyzer for testing.

18. The method of claim 17 comprising additional step of purging said closed storage container after each said opening for sample removal and before transfer of another sample to said closed storage container.

19. The method of claim 16 including the step of removing water from said storage container to a heavy water analyzer for testing.

20. The method of claim 16 comprising additional step of purging said closed storage container after each said opening for sample removal and before transfer of another sample to said closed storage container.

21. The method of claim 14 wherein said specified depths are selected based upon the hydrostatic pressures within said water wells at these depths.

* * * * *